(12) United States Patent
Bangert et al.

(10) Patent No.: US 8,101,366 B2
(45) Date of Patent: Jan. 24, 2012

(54) ASSESSMENT OF PATIENTS WITH SEPSIS TO DETERMINE A REQUIREMENT FOR THERAPEUTIC INTERVENTION WITH AN ANTI-INFLAMMATORY AND/OR ANTICOAGULATORY AGENT

(75) Inventors: Kristian Bangert, Holte (DK); Lars Otto Uttenthal, Salamanca (ES)

(73) Assignee: AntibodyShop A/S, Gentofte (DK)

( * ) Notice: Subject to any disclaimer, the term of this patent is extended or adjusted under 35 U.S.C. 154(b) by 154 days.

(21) Appl. No.: 12/517,085

(22) PCT Filed: Dec. 19, 2007

(86) PCT No.: PCT/DK2007/050194
§ 371 (c)(1),
(2), (4) Date: Sep. 8, 2009

(87) PCT Pub. No.: WO2008/074330
PCT Pub. Date: Jun. 26, 2008

(65) Prior Publication Data
US 2010/0047832 A1    Feb. 25, 2010

Related U.S. Application Data

(60) Provisional application No. 60/876,059, filed on Dec. 20, 2006.

(51) Int. Cl.
*G01N 33/53* (2006.01)
(52) U.S. Cl. ............................ 435/7.1; 435/7.2; 436/518
(58) Field of Classification Search .................... None
See application file for complete search history.

(56) References Cited

OTHER PUBLICATIONS

Siegel et al. (New England Journal Medicine 2002 vol. 347, p. 1030-1034).*
Warren et al. (New England Journal Medicine 2002 vol. 347, p. 1027-1030).*
Creasey et al. 1993 Clin Investigation vol. 91, p. 2850-2860.*
Levi et al. 2007 Am. J. Respir Crit Care Med. vol. 176, p. 483-490.*
Pastores 2003 Postgrad Med J. vol. 79, p. 5-10.*
Fourrier et al. 1993 Chest vol. 104, p. 882-888; Schumer 1976 Annual Meeting of the American Surgical Association, New Orleans, Louisiana, Apr. 7-9.*
Alcaraz et al., Thrombosis Research, vol. 79, No. 1, "Activation of the protein C pathway in acute sepsis", pp. 83-93, 1995.
Bernard G.R. et al., Critical Care 7, "Safety assessment of drotrecogin alfa (activated) in the treatment of adult patients with severe sepsis", pp. 155-163, 2003.
Bernard Gr et al., N.Engl. J. Med. 344, "Efficacy and safety of recombinant human activated protein C for severe sepsis", pp. 699-709, 2001.
Dahlback et al., J. Thromb. Haemost , "Molecular recognition in the protein C anticoagulant pathway (review)", pp. 1525-1534, 2003.
De Kleijn Ester et al., Crit Care Med, vol. 31, No. 6, "Activation of protein C following infusion of Protein C concentrate in children with severe meningococcal sepsis and purpura fulminans: a randomized, double-blinded placebo-controlled, dose-finding study", pp. 1839-1847, 2003.
Eli Lilly, Jun. 23, 2005, XIGRIS p. 1-10—XP002471124.
Esmon CT, Maturitas 47, Crosstalk between inflammation and thrombosis, pp. 305-314, 2004.
Espana F. et al., Blood 77, "In vivo and in vitro complexes of activated protein C with two inhibitors in baboons", pp. 1754-1760, 1991.
Faust SN et al., N. Engl. J. Med 345, "Dysfunction of endothelial protein C activation in severe meningococcal sepsis", pp. 408-416, 2001.
FDA, Nov. 21, 2001, XP002471120.
Gruber A. et al., Blood 79, "Direct detection of activated protein C in blood from human subjects", pp. 2340-2348, 1992.
Kinasewitz et al., Critical Care, vol. 8, No. 2, "Universal changes in biomarkers of coagulation and inflammation occur in patients with severe sepsis, regardless of causative micro-organism", pp. R82-R90, 2004.
Knaus WA et al., Crit Care Med. 13, APACHE II: a severity of disease classification system, pp. 818-829, 1985.
Laurel M. et al., Blood 76, "Turnover of *I-protein C inhibitor and *I-alpha 1-antitrypsin and their complexes with activated protein C", pp. 2290-2295, 1990.
Liaw et al., Blood, vol. 14, "Patients with severe sepsis vary markedly in their ability to generate activated protein C", pp. 3958-3964, 2004.
Liaw PC., Crit Care Med. 32 (5 Suppl.), Endogenous protein C activation in patients with severe sepsis (review), pp. 214-218, 2004.
Macias WL et al., Clin Pharmacol Ther 72, "Pharmacokinetic-pharmacodynamic analysis of drotrecogin alfa (activated) in patients with severe sepsis", pp. 391-402, 2002.
Marlar RA et al., Thromb Haemost 69, "Contribution of plasma proteinase inhibitors to the regulation of activated protein C in plasma", pp. 16-20, 1993.
Strandberg et al., Thrombosis and Haemostasis 86, "A sensitive immunochemical assay for measuring the concentration of the activated protein C-protein C inhibitor complex in plasma", pp. 604-610, 2001.
Strandberg K. et al., Thromb Haemost 89, "Stabilyte tubes that contain strongly acidic citrate prevent in vitro complex formation between activated protein C and protein C inhibitor", pp. 947-949, 2003.
Taylor et al., Journal of Thrombosis and Haemostasis 2, "Activated Protein C in sepsis", pp. 708-717, 2004.
Taylor F.B., J.Clin. Invest, vol. 79, "Protein C prevents the coagulopathic and lethal effects of *Escherichia coli* infusion in the baboon", pp. 918-925, 1987.
Mesters et al., "Prognostic Value of Protein C Concentrations in Neutropenic Patients at High Risk of Severe Septic Complications," *Crit. Care. Med.* 28:2209-2216, 2000.
European Patent Office Communication Pursuant to Article 94(3) EPC for European Application No. 07 846 454.2, dated Nov. 25, 2010.

* cited by examiner

*Primary Examiner* — Jacob Cheu
(74) *Attorney, Agent, or Firm* — Clark & Elbing LLP

(57) ABSTRACT

Methods of selecting patients with sepsis for treatment with an anti-inflammatory and/or anticoagulatory agent are provided.

19 Claims, No Drawings

ASSESSMENT OF PATIENTS WITH SEPSIS TO DETERMINE A REQUIREMENT FOR THERAPEUTIC INTERVENTION WITH AN ANTI-INFLAMMATORY AND/OR ANTICOAGULATORY AGENT

This application is a non-provisional of U.S. Provisional Patent Application No. 60/876,059, filed 20 Dec., 2006, which is hereby incorporated by reference in its entirety.

FIELD OF THE INVENTION

The present invention relates to methods of diagnosing and monitoring human disease by means of measurement in plasma of a complex of activated protein C (APC) and protein C inhibitor (PCI), hereinafter referred to as APC-PCI, the concentration of which indicates either inappropriately low activation of protein C (PC) or a high level of activation of PC in conditions giving rise to the systemic inflammatory response syndrome (SIRS). This is especially relevant to patients with sepsis, severe sepsis or septic shock, in which an inappropriately low activation of PC may provide an indication for therapeutic intervention by the intravenous administration of APC or other anti-inflammatory and/or anti-coagulatory agents. As such, the invention is relevant to the field of internal medicine, especially to critical or intensive care medicine, infectious disease medicine, and to surgery in relation to sepsis following operation or trauma.

Definitions

Systemic inflammatory response syndrome (SIRS): The consequences of systemic activation of the inflammatory system resulting in two or more of the following signs: heart rate >90 beats per minute, body temperature <36° C. or >38° C., respiratory rate >20 breaths per minute or a $P_aCO_2$<32 mm Hg, white blood cell count $<4 \times 10^9$ or $>12 \times 10^9$ cells/L or the presence of >10% immature neutrophils.

Sepsis: SIRS in which infection is highly suspected or proven.

Severe sepsis: Sepsis associated with new organ dysfunction, hypotension, or hypoperfusion.

Septic shock: Sepsis with acute circulatory failure unexplained by other causes, resulting in persistent arterial hypotension (systolic blood pressure <90 mm Hg or decreased >40 mm Hg from baseline despite fluid resuscitation).

BACKGROUND OF THE INVENTION

In recent years, the possibilities of therapeutic intervention in sepsis have been augmented by the development biological therapeutic agents that modulate the systemic activation of the inflammatory and coagulatory systems. Two such therapeutic agents are human APC, prepared by recombinant DNA technology, and antithrombin, purified from human plasma. Both agents show anti-coagulatory and anti-inflammatory activity in in vitro test systems or animal models. However, the results of treating unselected patients with sepsis with these agents have been either marginal (APC) or undetectable (antithrombin) in terms of increasing survival. In the case of APC, a beneficial effect on survival was seen in only the group of patients with severe sepsis and an APACHE II score of 25 or more (Bernard et al., 2001). APACHE II is a severity-of-disease classification system which uses a point score based upon initial values of 12 routine physiologic measurements, age, and previous health status to provide a general measure of severity of disease, resulting in a score ranging from 0 to 71 that correlates with the risk of hospital death (Knaus et al., 1985).

The problem is therefore how to improve the selection of patients with sepsis for treatment with APC so that those patients who are most likely to benefit from this treatment receive it, and those who are unlikely to benefit do not. The latter consideration is important, because the administration of APC is both costly and associated with unwanted effects, in particular with an increased incidence of serious bleeding events, including intracranial hemorrhage. While selecting patients for treatment by means of the APACHE II score goes some way towards such a selection, it is the purpose of the present invention to provide an improved method of selecting patients for APC treatment based on demonstrating the patient's requirement for APC by measuring an insufficient activation of endogenous PC. This may select patients for treatment although they have an APACHE II score <25 and may also exclude patients with an APACHE score $\geq 25$ because they already show an appropriate level of activation of endogenous PC.

PC is a protein synthesized in a vitamin-K-dependent manner by the liver as a single polypeptide chain of 461 amino acid residues. It is cleaved into a light chain of 155 amino acid residues linked by a single disulfide bridge to a heavy chain of 262 amino acid residues, both chains being glycosylated. The protein is a serine protease zymogen with an active site in the heavy chain protected by an N-terminal peptide, which is split off during activation. Mature PC has a molecular mass of approximately 62 kDa and is approximately 23% glycosylated. Its concentration in plasma is 3-5 µg/mL and its half-life in the circulation is 6-8 hours. PC is slowly activated by thrombin and 1000-fold more rapidly activated by thrombin in complex with the receptor, thrombomodulin, at the vascular surface of endothelial cells. Here the activation of PC is further 20-fold enhanced by the binding of PC to the endothelial PC receptor (EPCR). PC can also be activated pharmacologically by serine proteases from *Agkistrodon* snake venom.

APC generated by activation of PC is a serine protease which splits blood coagulation factors Va and VIIIa, using protein S and blood coagulation factor V as cofactors. It thereby limits blood coagulation in the vicinity of membrane-bound factors Va and VIIIa. APC may also have an indirect fibrinolytic activity by inhibiting plasminogen activator inhibitor-1 and by limiting the generation of activated thrombin-activatable fibrinolysis inhibitor. APC may also have an anti-inflammatory action by inhibiting the production of tumor necrosis factor by monocytes, by blocking the adhesion of leukocytes to selecting, and by limiting thrombin-induced endothelial inflammatory responses. In addition, it has been demonstrated to have an inhibitory effect on apoptosis.

APC has a molecular mass of approximately 55 kDa and its normal concentration in plasma has been estimated as lying within the range of 1-3 ng/mL (1.19 ±standard deviation 0.41 ng/mL). The half-life of APC in the human circulation is short, being variously estimated as 20 minutes (Dahlback and Villoutreix, 2003) or 45 minutes (Macias W L et al., 2002). During constant intravenous infusion a steady state concentration is reached after 2 hours, and when infusion is stopped, the concentration of APC in plasma falls to below 10 ng/mL within 2 hours. Endogenous plasma concentrations of APC measurable by the hitherto used immunoenzymatic assay (Gruber and Griffin, 1992) exceed the detection limit normally achieved in practice (10 ng/mL) in only 3.3% of patients with sepsis.

As soon as APC is produced within the circulation, it undergoes inactivation by reacting with serpins (serine protease inhibitors) also present in the blood. These include PCI, alpha$_1$-antitrypsin (AAT), alpha$_2$-antiplasmin and C1-esterase inhibitor (in descending order of second order rate constants). Of these, PCI appears to be of greatest physiologic importance. PCI is a single-chain protein of molecular mass about 57 kDa, and its normal concentration in plasma is about 5 µg/mL. Its half-life in the circulation, measured in rabbits, is about 24 hours (Laurell et al., 1990). APC-PCI complexes are formed with a second order rate constant of $13 \times 10^3$ $M^{-1}s^{-1}$ (Marlar R A et al., 1993) and their half-life in the circulation is about 20 minutes in rabbits (Laurell et al., 1990), 40 minutes in baboons (Espana F et al., 1991). AAT is a single chain protein of molecular mass about 54 (50-60) kDa, and its normal concentration in plasma is about 2.5 mg/mL, about 500-fold higher than that of PCI. Its half-life in the circulation measured in rabbits is 62 hours (Laurell et al., 1990). APC-AAT complexes are formed with a second order rate constant of 15 $M^{-1}s^{-1}$ (Marlar et al., 1993) and their half-life in the circulation is 72 minutes in rabbits (Laurell et al., 1990), 140 min in baboons (Espana et al., 1991).

It will be seen that the rate constant for APC-AAT complex formation is only about one thousandth of that for APC-PCI complex formation, but this is partially compensated for by the 500-fold higher concentration of AAT than PCI in plasma. At the same time, the half-life of APC-AAT complexes in the circulation is 3- to 4-fold longer than that of APC-PCI complexes. This results in higher concentrations of APC-AAT complexes in plasma than APC-PCI complexes.

APC can also form complexes with alfa$_2$-antiplasmin, with a second order rate constant of 410 $M^{-1}s^{-1}$, or very slowly with C1-esterase inhibitor (second order rate constant of <6 $M^{-1}s^{-1}$). The possible formation of these complexes is not regarded as being physiologically significant.

The median plasma concentration of APC-PCI complex, from blood collected from healthy volunteers into 5-ml vacuum tubes containing 0.5 mL of 0.5 M citrate buffer, pH 4.3, to prevent further complex formation after sampling, is 0.13 ng/mL, with a range of 0.07-0.26 ng/mL (Strandberg et al., 2003). In 18 patients with sepsis the mean concentration of APC-PCI complex in plasma (containing 50 mM benzamidine as an inhibitor of further complex formation) was 3 ng/mL±standard deviation (SD) 2 ng/mL, estimated by enzyme-linked immunosorbent assay (Alcaraz et al., 1995). The mean concentration of APC-AAT complex in these patients was 26 ng/mL±SD 15 ng/ml. The mean level of PC in plasma on day 1 was 69%±SD 28% of the mean normal control value, and the mean level of PCI was 33%±22% of the control value, showing consumption of these components due to activation of PC in sepsis.

Patients with severe sepsis vary markedly in their ability to generate APC (Liaw et al., 2004). The endothelial receptors essential for efficient activation of PC, thrombomodulin and EPCR may be down-regulated in sepsis. For example, the levels of thrombomodulin and EPCR are reduced in the endothelium of children with severe meningococcal sepsis (Faust et al., 2001), and in vitro studies have shown that thrombomodulin and the EPCR are down-regulated by inflammatory cytokines (Esmon, 2004). The extent of this down-regulation is variable, and this means that some patients with sepsis show low levels of endogenous APC as measured by an improved version of the immunoenzymatic assay, a phenomenon that does not correlate with the APACHE II score (Liaw, 2004).

SUMMARY OF THE INVENTION

We have invented a method of selecting patients with sepsis for APC treatment which is expected to be more effective in avoiding inappropriate treatment than using the APACHE II score alone as described above. The new method is based on the consideration that APC administration is unlikely to benefit patients who already have a raised activation of endogenous PC, and on the new observation that sepsis patients who show no increase in PC activation have a higher mortality than sepsis patients as a whole.

In a preferred embodiment, the method comprises determining the state of activation of native PC in a patient with sepsis by the steps of i) taking a blood sample from the patient into a tube containing an agent that prevents the formation of further APC-PCI complex after sampling, ii) separating the plasma, iii) measuring the concentration of APC-PCI complex in the plasma, iv) comparing said concentration with a cutoff value corresponding to the upper limit of APC-PCI concentrations found in plasma samples from healthy individuals multiplied by a correction factor of value between 0.75 and 1.5, wherein a concentration below the cutoff value demonstrates a failure of appropriate activation of endogenous PC and provides an indication for treatment by the administration of exogenous APC.

The need to apply a corrective multiplication factor between 0.75 and 1.5 to calculate the cutoff value from the upper limit of values found in healthy individuals depends on the method of measurement used and the value of the correction factor is empirically determined by the results of a clinical validation of the measurement method on patients with sepsis and on healthy volunteers.

Whole blood can also be used in the above general method, depending on the technical details of the method used to measure the concentration of APC-PCI in the plasma.

If, in addition to the plasma APC-PCI concentration, the APACHE II score is taken into account, then patients who have both a plasma APC-PCI concentration lower than the cutoff value and an APACHE II score $\geq 25$ have a very high mortality, the deaths occurring in this sub-subgroup accounting for the vast majority of the deaths in the subgroup with plasma APC-PCI values below the cutoff. This sub-subgroup of patients should be especially considered for treatment by the administration of exogenous APC. As indicated by data given below, by confining APC administration to this sub-subgroup of patients, the number of patients that have to be treated in order to save one life is reduced to one third of that found when patients are selected for treatment by APACHE II score alone. At the same time, if exogenous APC administration has little or no beneficial effect when endogenous PC is already appropriately activated, it is not expected that any lives will be lost as a consequence of not treating patients with raised plasma APC-PCI concentrations. Selecting sepsis patients for APC treatment in this way can be expected to bring about an up to 3-fold improvement in the benefit-to-cost relation as compared with selecting patients by APACHE II score alone.

It will apparent that this method of selecting patients with sepsis for APC treatment does not depend on any particular method of measuring the state of endogenous PC activation. This can be quantified by measuring endogenous APC in blood or plasma, whether by an immunochemical, immunoenzymatic or any other method, or by measuring any complex formed by an inhibitor with the endogenously generated APC, whether the inhibitor is a serpin such as PCI, AAT or another serpin, or any other molecule capable of binding APC. Nor does the method depend on any particular way of measuring the APC-inhibitor complex. In each case, the cutoff value is determined by multiplying by a factor lying between 0.75 and 1.5 the upper limit of values obtained by applying the chosen method to samples from healthy individuals without known clotting disorders. In a preferred embodiment, the state of PC activation is determined by measuring the concentration in a plasma sample of APC-PCI complex by an immunochemical method.

DETAILED DESCRIPTION OF THE INVENTION

In a preferred embodiment of the invention, we have developed an immunochemical method for determining the concentration of APC-PCI complex in plasma, and used this to measure APC-PCI complex in 135 consecutive patients admitted to a hospital intensive care unit. The results of this study are given in Example 1 below. We have surprisingly found that the subgroup of patients with sepsis, who during hospitalization showed no activation of PC sufficient to produce a concentration of APC-PCI complex in plasma equal to or greater than a value close to the upper limit of normal, had a higher mortality than that of all sepsis patients. The cutoff value giving optimal discrimination between patients of higher and lower mortality was close to the upper limit of normal, and could be defined in terms of the upper limit of normal concentrations multiplied by a factor close to 1. The subgroup of patients who during hospitalization showed a moderate activation of PC had a lower mortality than that of all sepsis patients. On the other hand, the subgroup of patients who during hospitalization showed a high activation of PC, again had a higher mortality than that of all sepsis patients.

The study indicates that non-activation of PC in sepsis, as evidenced by maximal plasma concentrations of APC-PCI complex equal to or below the cutoff value, represents the failure of an appropriate, protective PC activation response and is hence also associated with a raised relative mortality. When PC activation is appropriate, as reflected by a moderate elevation of plasma concentrations of APC-PCI complex, the relative mortality is reduced.

We therefore propose that those patients with sepsis whose plasma concentrations of APC-PCI complex remain within the normal range (or below the upper limit of normal multiplied by an empirically determined correction factor) are those who should be treated by the intravenous administration of APC. According to the results of the study described in Example 1, this procedure should offer the possibility, in the best case, of a reduction in mortality from 44% to 13%, on the extreme assumption that the lower mortality of the subgroup with moderate PC activation than that of the subgroup without PC activation is entirely due to the effects of APC in the circulation. The proportionate contribution of APC to the totality of possible mortality-reducing influences will determine what reduction in mortality can be obtained in practice.

If, in addition to the plasma APC-PCI concentration, the APACHE II score is taken into account, by far the highest mortality in any subgroup of sepsis patients was observed in the sub-subgroup without PC activation and an APACHE II score $\geq 25$. This sub-subgroup had a very high mortality (71%).

We therefore further propose that those patients with sepsis whose plasma concentrations of APC-PCI complex remain equal to or below the cutoff value and who have an APACHE II score $\geq 25$ are those who should be specially considered for treatment by the intravenous administration of APC. According to the results of the study, if it assumed that the lower mortality of the subgroup with moderate PC activation than that of the subgroup without PC activation is entirely due to the effects of APC in the circulation, this should offer the possibility, in the best case, of reducing the mortality of this sub-subgroup of patients from 71% to 25%.

A major possible advantage of selecting sepsis patients for APC treatment on the basis of low APC-PCI levels and an APACHE II score $\geq 25$ is that the number of patients that have to be treated in order to save one life can be expected to fall dramatically in comparison with the number selected for treatment on the basis of the APACHE II score alone. In the group of sepsis patients studied, 22 would have been selected for APC treatment on the basis of the APACHE II score. 10 of these patients died. On the assumption that APC-treatment would be totally effective in preventing these deaths regardless of the state of endogenous PC activation, the best case calculation is that 2.2 (22/10) patients would have to be treated to save one life. There were 5 deaths in the sub-subgroup of 7 patients without PC activation and with an APACHE II score $\geq 25$. If it is assumed that APC treatment is only effective, but totally effective, in patients without endogenous PC activation, 4.4 (22/5) patients would have to be treated to save one life. However, if APC treatment is confined to the sub-subgroup of patients without PC activation and with an APACHE II score $\geq 25$, only 1.4 (7/5) patients would have to be treated to save one life, on the same assumptions. Overall, these calculations indicate that selecting patients on the basis of low APC-PCI and APACHE II score $\geq 25$ as opposed to selecting by APACHE II score alone may reduce the number of patients treated to save one life to about one third, if APC is only effective in patients without endogenous PC activation. This represents a 3-fold improvement in the cost-effectiveness of a generally applied APC treatment policy. The same improvement in cost-effectiveness would also apply if the beneficial effects of APC treatment were only partial, as is indeed likely to be the case. Furthermore, if the assumption is in fact true that APC administration is of no benefit if there is adequate activation of endogenous PC, then no additional deaths are to be expected as a consequence of non-treatment of the excluded patients; on the contrary, the side effects of inappropriate APC administration to achieve supra-pathological levels will be avoided in a large number of patients. These side effects include bleeding episodes, including intracranial hemorrhage with consequent neurological deficit.

Accordingly, the present invention relates to determining the state of PC activation in a patient with sepsis by measuring a biomarker molecule indicative of said state in a sample of plasma from the patient. If the concentration of the biomarker does not exceed a cutoff value equal to the upper limit of the range of concentrations found in plasma from healthy volunteers without known coagulation disorders, multiplied by an empirically determined correction factor between 0.75 and 1.5, such as between 0.8 and 1.4, such as between 0.85 and 1.3, such as between 0.9 and 1.2, such as between 0.0.95 and 1.1, the state of PC activation is determined to be inappropriately low and this provides a prima facie indication for treatment of the patient by administering exogenous APC. It also indicates that the patient has a higher mortality risk than the generality of patients with sepsis. If a patient with an inappropriately low state of PC activation also has an APACHE II score $\geq 25$, this further strengthens the indication for APC administration and places the patient in a category with a very high mortality.

The method of the present invention in one embodiment comprises the steps of measuring the concentration of APC-PCI complex in a sample of plasma from the patient with sepsis, and comparing the measured concentration with a selected cutoff value determined to equal the upper limit of those plasma concentrations found in humans that have no known current disease, hereinafter called normal values, multiplied by an empirically determined correction factor as defined above. By the methodology of the present study, the value of the correction factor that gave the most discriminating cutoff value was determined to be 0.96, but other analytical methods and other patient populations may lead to the determination of a slightly different correction factor. However, in all cases, theoretical considerations lead to an expectation that the correction factor will be close to unity. The upper limit of normal values is defined for this purpose as the least value below which 97.5% of the normal values fall. If the measured APC-PCI concentration is below the cutoff level, this is an indication that the patient has an inappropriate failure of PC activation in response to sepsis.

The cutoff level below which the plasma level of APC-PCI complex is indicative of failure of PC activation can vary with the technique of measurement of APC-PCI complex and is preferably a level of 0.20 ng/mL or more, such a value between 0.20 ng/mL and 0.41 ng/mL, such as 0.21 ng/mL, or 0.22 ng/mL, or 0.23 ng/mL, or 0.24 ng/mL, or 0.25 ng/mL, or 0.26 ng/mL, or 0.27 ng/mL, or 0.28 ng/mL or 0.30 ng/mL, or 0.35 ng/mL, or 0.40 ng/mL.

A further aspect of the present invention is that the method can be used to monitor the course of the PC activation response to sepsis, or the rise and fall in APC-PCI levels after the administration of exogenous APC, or the response to another treatment of sepsis which is not APC administration. The intervals at which samples of blood are taken for monitoring of the plasma level can be as short as the physician considers appropriate, but monitoring of endogenous APC-PCI levels in plasma from patients that have not been given exogenous APC is preferably carried out at intervals not longer than 24 hours. For monitoring the APC-PCI levels after APC administration or other treatments, shorter intervals down to a suggested period of 1 hour or even shorter may be used as the physician determines.

A further aspect of the present invention is that when endogenous APC-PCI levels are determined, levels above a second, higher cutoff value will also be predictive of a higher mortality than the generality of sepsis patients. This second, higher cutoff level above which the mortality is raised, is preferably a level of 0.70 ng/mL or more, such a value between 0.70 ng/mL and 1.05 ng/mL, such as 0.71 ng/mL, or 0.72 ng/mL, or 0.73 ng/mL, or 0.74 ng/mL, or 0.75 ng/mL, or 0.80 ng/mL, or 0.85 ng/mL, or 0.90 ng/mL or 0.95 ng/mL, or 1.00 ng/mL.

As endogenous APC-PCI levels indicate the status of PC activation in the patient, it is evident that raised levels of other biomarkers of PC activation that exceed a similarly determined second, higher cutoff value will also be predictive of a higher mortality than the generality of sepsis patients.

Measurement of APC-PCI complex in a sample of plasma can be performed by any method that provides satisfactory analytical specificity, sensitivity and precision. Preferred methods are binding assays using one or more binding molecules specific to the components of human APC-PCI. Such binding molecules include, but are not limited to, polyclonal or monoclonal antibodies against neoepitopes on the APC-PCI complex, or against PCI or PCI reacted with a serine protease, and PC or APC, or specific binding molecules for these components generated by other means.

In a preferred method, monoclonal antibodies raised against respectively PCI in complex with a serine protease and against PC are used. The first antibody is linked to a solid support to capture APC-PCI from the sample, while the other is linked to a label such as a dye complex, or fluorophore, or an electrochemically activated signaling group, or a paramagnetic group, or biotin or enzyme that can be detected by any of many methods known to those skilled in the art. The solid support may e.g. be a polystyrene or polyvinyl chloride surface for enzyme-linked immunosorbent assay (ELISA), or latex (polystyrene) or other particles, or a filter frit composed of compressed polyethylene particles, or a porous nitrocellulose matrix, or indeed any suitable support used in immunochemical analyses.

Plasma samples for the measurement of APC-PCI complex by the above methods must be prepared from blood collected into a receptacle that contains an anticoagulant agent which is preferably ethylenediaminetetraacetic acid (EDTA) or citrate, and an adequate amount of an agent that instantaneously prevents the further formation of APC-PCI complex in vitro, such as benzamidine or acid sodium citrate buffer, pH 4.3.

The following Example illustrates the diagnostic procedure of the invention as applied to a clinical study of unselected patients admitted to a hospital intensive care unit.

EXAMPLE 1

Clinical Study of Unselected Patients Admitted to Intensive Care

In a preferred embodiment of the invention, we have developed a sandwich enzyme-linked immunosorbent assay (ELISA) method (Example 2) for determining the concentration of APC-PCI complex in plasma, and used this to measure APC-PCI complex in 135 consecutive patients admitted to a hospital intensive care unit. 53 patients had sepsis at some stage during hospitalization (sepsis group) and 82 had not (non-sepsis group). The subgroup of patients with sepsis, who during hospitalization showed no activation of PC sufficient to produce a concentration of APC-PCI complex in plasma equal to or greater than a value close to the upper limit of normal, had a higher mortality (44%) than that of all sepsis patients (32%), showing a relative mortality of 136%. In this case, the cutoff value giving the optimal discrimination was found to be 0.25 ng/mL, close to the upper limit of normal values, which was 0.26 ng/mL. The factor with which the upper limit of normal had to be multiplied to find the best cutoff was therefore 0.25/0.26, or 0.96. The subgroup of patients who during hospitalization showed a moderate activation of PC, sufficient to bring the highest recorded concentration of APC-PCI complex in plasma into the range of 0.26-0.72 ng/mL, had a lower mortality (13%) than that of all sepsis patients, showing a relative mortality of 41%. On the other hand, the subgroup of patients who during hospitalization showed a high activation of PC, sufficient to bring the highest recorded concentration of APC-PCI complex in plasma above 0.72 ng/mL, had a higher mortality (50%) than that of all sepsis patients, showing a relative mortality of 156%.

In the group of patients without sepsis, there was a non-significant trend suggesting that raised mortality was associated with PC activation. The in-hospital mortality of patients without sepsis and with APC-PCI values within the normal range was 0%, while the mortality was 15% in those with either moderate or high PC activation. Patients without sepsis differed markedly from those with sepsis in that normal APC-PCI values were associated with a good prognosis in those without sepsis, but with a raised relative mortality in those with sepsis.

These data are summarized in Table 1.

TABLE 1

In-hospital absolute and relative mortalities of
the sepsis (n = 53) and non-sepsis (n = 82) groups of
patients admitted to intensive care, by PC activation subgroup

| PC activation subgroup | Group | Sepsis (deaths/n) | Non-sepsis (deaths/n) |
|---|---|---|---|
| No activation APC-PCI ≦0.25 ng/mL | Mortality | 43.8% (7/16) | 0.0% (0/14) |
|  | Relative mortality | 136.4% | 0.0% |
| Moderate activation APC-PCI 0.26-0.72 ng/mL | Mortality | 13.0% (3/23) | 14.7% (5/34) |
|  | Relative mortality | 40.7% | 120.6% |
| High activation APC-PCI >0.72 ng/mL | Mortality | 50.0% (7/14) | 14.7% (5/34) |
|  | Relative mortality | 155.9% | 120.6% |
| P ($\chi^2$) |  | 0.0319 | 0.3096 |

Relative mortality: (mortality of PC activation subgroup)/(overall mortality of group)

APACHE II scores were available for 51 patients in the sepsis group. If, in addition to the plasma APC-PCI concentration, the APACHE II score is taken into account, by far the highest mortality in any subgroup of sepsis patients was observed in the sub-subgroup without PC activation and an APACHE II score ≧25. This sub-subgroup had a mortality of 71%. The sub-subgroup without PC activation and an APACHE II score <25 had a mortality of only 11%. In sepsis patients with a moderate level of PC activation, the mortality associated with an APACHE II score ≧25 was 25%, while that associated with an APACHE II score <25 was 8%. In those with a high level of PC activation, APACHE II scores above or below 25 made no significant difference to the mortality (43% and 57% respectively).

These data are summarized in Table 2.

TABLE 2

In-hospital mortality of sepsis patients
admitted to intensive care, by APACHE II score and PC
activation subgroup

| PC activation subgroup | APACHE II score ≧25 Mortality (deaths/n) | APACHE II score <25 Mortality (deaths/n) | P (Fisher's exact, 2 tailed) | Total Mortality (deaths/n) |
|---|---|---|---|---|
| No activation APC-PCI ≦0.25 ng/mL | 71% (5/7) | 11% (1/9) | 0.049 | 38% (6/16) |
| Moderate activation APC-PCI 0.26-0.72 ng/mL | 25% (2/8) | 8% (1/13) | 0.632 | 14% (3/21) |
| High activation APC-PCI >0.72 ng/mL | 43% (3/7) | 57% (4/7) | 1.000 | 50% (7/14) |
| P ($\chi^2$) | 0.195 | 0.023 |  | 0.068 |
| Total | 45% (10/22) | 21% (6/29) |  | 31% (16/51) |

The following non-limiting examples illustrate how the concentration of APC-PCI complex may be measured in human plasma. Example 2 is the analytical method used in Example 1 above.

EXAMPLE 2

Determination of APC-PCI Complex in Plasma by Sandwich ELISA

APC-PCI complex for use as a standard and as calibrator material was prepared by a modification of the method described by Strandberg et al. (2001). Human recombinant activated protein C (Xigris; Ely Lilly) was incubated at room temperature with a 1.5-fold molar excess of purified human PCI purchased from the Department of Clinical Chemistry, University Hospital of Malmo, Sweden, in the buffer described by Strandberg et al. (2001). At timed intervals, the remaining APC activity was determined by a modification of the immunoenzymatic assay of Gruber and Griffin (1992). All detectable APC activity had disappeared by 1 hour. Glycerol was added to the preparation to a final concentration of 50% v/v and aliquots of the solution were stored at −135° C.

The capture antibody for PCI in complex with APC was derived from mouse "monoclonal" antibody M36, described by Strandberg et al. (2001) and the subject of U.S. Pat. No. 6,967,082 published Nov. 22, 2005, which is herewith incorporated into the present application by reference. The rights to use the antibody and the hybridoma cell line producing it were licensed from Forskarpatent i Syd AB, Lund, Sweden. The cell line actually produces two different antibodies against a neoepitope on reacted PCI, one being of subclass $IgG_{1\kappa}$ and the other of subclass $IgG_{2b\kappa}$. The cell line was subcloned by us and only cells producing the $IgG_{1\kappa}$ antibody used. This antibody was named JST 001-038. The detection antibody was biotinylated mouse monoclonal antibody HYB 237-05B, which reacts with both APC and PC.

Blood samples were collected from human subjects by venepuncture and drawn directly into 5-mL vacuum tubes, each containing 0.5 mL of 0.5 M citrate buffer, pH 4.3 (Stabilyte; Biopool, Umeå, Sweden). The plasma was separated by centrifugation at 4° C., and stored in aliquots at −80° C. until analyzed.

Polystyrene ELISA plates were coated overnight at 4° C. with antibody JST 001-038 at a concentration of 5 µg/mL in 0.05 M sodium carbonate buffer, pH 9.6, applied at 100 µL/well. The wells were emptied, washed 3 times with a wash buffer of phosphate-buffered saline, pH 7.4, containing 10 mM phosphate, 140 mM sodium chloride and 0.05% v/v Tween 20, and blotted. Calibrating solutions were prepared by diluting APC-PCI calibrator stock in dilution buffer (wash buffer containing 0.5% w/v bovine albumin and 0.006% w/v phenol red). Plasma samples were diluted in sample dilution buffer, pH 7.4 (10 mM phosphate, 200 mM sodium chloride, 0.25% v/v Tween 20, 0.5% w/v bovine albumin, irrelevant mouse monoclonal IgG1κ 10 µg/mL, bovine IgG 10 µg/mL, 0.006% w/v phenol red and 0.02% w/v thimerosal). Diluted calibrators and samples were applied to the wells in 100-µL volumes and incubated for 1 hour at room temperature on a shaking table. The wells were then emptied, washed and blotted as before. Biotinylated antibody HYB 237-05B at 0.5 µg/mL in dilution buffer was added to each well at 100 µL/well and incubated for 1 hour at room temperature on a shaking table. The wells were then emptied, washed and blotted as before. A complex of horseradish peroxidase and streptavidin (ZyMax; Invitrogen/Zymed, San Francisco, Calif.) at a dilution of 1/2000 in dilution buffer was added to each well at 100 µL/well and incubated for 1 hour at room temperature on a shaking table. The wells were then emptied, washed and blotted as before. A substrate solution containing tetramethylbenzidine and peroxide (TMB-Plus, Kem-En-Tech, Copenhagen, Denmark) was then applied to each well at 100 µL/well and incubated at room temperature in the dark for 30 minutes, after which the color reaction was stopped by adding 50 μL of 1 M sulfuric acid to each well. The light absorbances of the wells at a wavelength of 450 nm were then read in an ELISA plate reader, subtracting the light absorbances at 650 nm. The concentrations of NGAL in the samples were then calculated from the standard curve generated from the light absorbance readings of the calibrators of known concentration.

The assay had a range of 0.016 ng/mL to 1 ng/mL, with a detection limit (95% confidence limit of difference from zero) of 4 pg/mL. Plasma samples were routinely measured at a dilution of 1/10.

It will be evident to persons skilled in the art that many other methods of measuring APC-PCI complex in blood or plasma by means of binding molecules specific for either or both of the components of the complex can be devised, including methods suitable for rapid, near-patient analysis and methods suitable for automated, random-access central laboratory analyzers. For example, an immunofluorometric method has been described by Strandberg et al. (2001).

It will further be evident to persons skilled in the art that this method of selecting patients with sepsis for APC treatment does not depend on any particular method of measuring the state of endogenous PC activation. This can be quantified by measuring endogenous APC in plasma, whether by an immunochemical, immunoenzymatic or any other method, or by measuring any complex formed by a serpin with the endogenously generated APC, whether the serpin is PCI, AAT or another serpin capable of reacting with APC, or by measuring the complex formed by APC with any endogenous molecule that specifically binds to APC. Nor does the method depend on any particular way of measuring the complex of APC with a serpin or other binding molecule. In each case, the cutoff value is determined by the upper limit of values obtained by applying the chosen method to samples from healthy individuals without known clotting disorders, multiplied by an empirically determined correction factor. The state of endogenous PC activation can also be estimated, albeit with considerable uncertainty introduced by various confounding factors, by measuring the total amount of PC and/or PCI in blood or plasma and comparing this with a cutoff value derived from the respective mean normal blood or plasma concentrations of these proteins, multiplied by an empirically determined factor. It will then be assumed that levels of these proteins below the respective cutoff levels will indicate a degree of PC activation.

REFERENCES

Alcaraz A, Espana F, Sanchez-Cuenca J, Zuazu I, Estelles A, Aznar J, Vicente V (1995) Activation of the protein C pathway in acute sepsis. Thromb Res 79:83-93.
Bernard G R, Vincent J L, Laterre P F, LaRosa S P, Dhainaut J F, Lopez-Rodriguez A, Steingrub J S, Garber G E, Helterbrand J D, Ely E W, Fisher C J Jr; Recombinant human protein C Worldwide Evaluation in Severe Sepsis (PROWESS) study group (2001) Efficacy and safety of recombinant human activated protein C for severe sepsis. N Engl J Med 344:699-709.
Dahlback B, Villoutreix B O (2003) Molecular recognition in the protein C anticoagulant pathway (review). J Thromb Haemost 1:1525-1534.
Esmon C T (2004) Crosstalk between inflammation and thrombosis (review). Maturitas 47:305-314.
Espana F, Gruber A, Heeb M J, Hanson S R, Harker L A, Griffin J H (1991) In vivo and in vitro complexes of activated protein C with two inhibitors in baboons. Blood 77:1754-1760.
Faust S N, Levin M, Harrison O B, Goldin R D, Lockhart M S, Kondaveeti S, Laszik Z, Esmon C T, Heyderman R S (2001) Dysfunction of endothelial protein C activation in severe meningococcal sepsis. N Engl J Med 345:408-416.
Gruber A, Griffin J H (1992) Direct detection of activated protein C in blood from human subjects. Blood 79:2340-2348.
Knaus W A, Draper E A, Wagner D P, Zimmerman J E (1985) APACHE II: a severity of disease classification system. Crit Care Med 13:818-829.
Laurell M, Stenflo J, Carlson T H (1990): Turnover of *I-protein C inhibitor and *I-alpha 1-antitrypsin and their complexes with activated protein C. Blood 76:2290-2295.
Liaw P C (2004) Endogenous protein C activation in patients with severe sepsis (review). Crit Care Med 32(5 Suppl): S214-S218.
Liaw P C, Esmon C T, Kahnamoui K, Schmidt S, Kahnamoui S, Ferrell G, Beaudin S, Julian J A, Weitz J I, Crowther M, Loeb M, Cook D (2004) Patients with severe sepsis vary markedly in their ability to generate activated protein C. Blood 104:3958-3964.
Macias W L, Dhainaut J F, Yan S C, Helterbrand J D, Seger M, Johnson G 3rd, Small D S (2002). Pharmacokinetic-pharmacodynamic analysis of drotrecogin alfa (activated) in patients with severe sepsis. Clin Pharmacol Ther 72:391-402.
Marlar R A, Kressin D C, Madden R M (1993) Contribution of plasma proteinase inhibitors to the regulation of activated protein C in plasma. Thromb Haemost 69:16-20.
Strandberg K, Kjellberg M, Knebel R, Lilja H, Stenflo J (2001) A sensitive immunochemical assay for measuring the concentration of the activated protein C-protein C inhibitor complex in plasma: Use of a catcher antibody specific for the complexed/cleaved form of the inhibitor. Thromb Haemost 86:604-610.
Strandberg K, Svensson A, Stenflo J (2003) Stabilyte tubes that contain strongly acidic citrate prevent in vitro complex formation between activated protein C and protein C inhibitor. Thromb Haemost 89:947-949.

The invention claimed is:

1. A method of determining whether or not a patient with sepsis should be treated by the administration of activated protein C or other anticoagulant or anti-inflammatory agent, said method comprising the steps of
  i) determining in a sample of plasma or whole blood from the patient the concentration of a complex of activated protein C and an endogenous serpin that binds to activated protein C, and
  ii) comparing said concentration with a predetermined first cutoff value corresponding to the upper limit of normal concentrations of said complex in samples of plasma or whole blood from healthy individuals, wherein a concentration below the first cutoff value a) indicates a higher mortality than average for patients with sepsis, and b) provides an indication for said treatment.

2. The method of claim 1, wherein the endogenous serpin that binds to activated protein C is protein C inhibitor.

3. The method of claim 2, wherein the first cutoff value in plasma is 0.20 ng/mL or more.

4. The method of claim 1 further comprising determining an APACHE II (Acute Physiology and Chronic Health Evaluation II) score of the patient, wherein an APACHE II score equal to or greater than 25 coexisting with a concentration of the complex of activated protein C and endogenous serpin that binds to activated protein C below the first cutoff value is indicative of a) a much higher mortality than average for patients with sepsis, and b) a strong indication for treatment of the patient by the administration of exogenous activated protein C or other anticoagulant or anti-inflammatory agent.

5. The method of claim 1, further comprising repeating steps i) and ii) one or more times.

6. The method of claim 5, wherein repeating steps i) and ii) is performed within 24 hours.

7. The method of claim 5, wherein repeating steps i) and ii) is performed after a treatment of the patient with sepsis has been initiated or completed.

8. The method of claim 5, wherein the endogenous serpin that binds to activated protein C is protein C inhibitor.

9. A method of determining that the degree of protein C activation in a patient with sepsis is so high as to be independently predictive of a higher mortality than average for patients with sepsis, said method comprising the steps of
  i) determining the concentration of a complex of activated protein C with an endogenous serpin that binds to activated protein C indicative of protein C activation in a sample of plasma or whole blood from the patient, and
  ii) comparing said concentration with a second cutoff value, said second cutoff value being chosen to exclude a moderate activation of endogenous protein C associated with a lower than average mortality for patients with sepsis, wherein a concentration above the cutoff value is indicative of a higher than average mortality for patients with sepsis.

10. The method of claim 9, wherein the endogenous serpin that binds to activated protein C is protein C inhibitor.

11. The method of claim 10, wherein said second cutoff value is 0.70 ng/mL or more.

12. The method of claim 1, wherein the complex of activated protein C and endogenous serpin that binds to activated protein C is measured by means of one or more molecules that bind specifically to a neoepitope on the complex, or to the binding protein or a neoepitope on said binding protein, or to the protein C component of the complex.

13. The method of claim 9 wherein the complex of activated protein C and endogenous serpin that binds to activated protein C is measured by means of one or more molecules that bind specifically to a neoepitope on the complex, or to the binding protein or a neoepitope on said binding protein, or to the protein C component of the complex.

14. The method of claim 1, wherein the endogenous serpin that binds to activated protein C is alpha$_1$-antitrypsin (AAT).

15. The method of claim 5, wherein the endogenous serpin that binds to activated protein C is alpha$_1$-trypsin (AAT).

16. The method of claim 1, wherein said determining step i) comprises measuring the concentration of said complex in said sample.

17. The method of claim 1, wherein said determining step i) comprises determining the concentration of said complex in said sample using a molecule that binds said activated protein C, said endogenous serpin protein, or both.

18. The method of claim 17, wherein said molecule is an antibody.

19. The method of claim 1 further comprising treating said patient with said APC or said other agent with similar effect or effects thereof.

* * * * *

UNITED STATES PATENT AND TRADEMARK OFFICE
CERTIFICATE OF CORRECTION

| | | |
|---|---|---|
| PATENT NO. | : 8,101,366 B2 | Page 1 of 1 |
| APPLICATION NO. | : 12/517085 | |
| DATED | : January 24, 2012 | |
| INVENTOR(S) | : Bangert et al. | |

It is certified that error appears in the above-identified patent and that said Letters Patent is hereby corrected as shown below:

In the Specifications:

Column 2, Line 50, replace "selecting" with --selectins--.

Signed and Sealed this
Fourth Day of December, 2012

David J. Kappos
*Director of the United States Patent and Trademark Office*